United States Patent [19]

Padmanathan

[11] Patent Number: 5,714,607
[45] Date of Patent: Feb. 3, 1998

[54] PROCESS IMPROVEMENT IN THE SYNTHESIS OF N-[3-(3-CYANO-PYRAZOLO [1,5-A]PYRIMIDIN-7-YL)PHENYL]-N-ETHYLACETAMIDE

[75] Inventor: Thurairajah Padmanathan, Piscataway, N.J.

[73] Assignee: American Cyanamid Company, Madison, N.J.

[21] Appl. No.: 758,132

[22] Filed: Nov. 25, 1996

Related U.S. Application Data

[60] Provisional application No. 60/007,859 Dec. 1, 1995.
[51] Int. Cl.$^6$ ................................................. C07D 487/04
[52] U.S. Cl. .................................................... 544/281
[58] Field of Search .................................... 544/281

[56] References Cited

U.S. PATENT DOCUMENTS 4,626,538   12/1986   Dusza et al. ........................... 544/281

*Primary Examiner*—John M. Ford
*Attorney, Agent, or Firm*—Arthur G. Seifert

[57] ABSTRACT

The invention is a process improvement for producing N-[3-(3-cyano-pyrazolo[1,5-a]pyrimidin-7-yl)phenyl]-N-ethyl-acetamide which is useful as an anxiolytic, antiepileptic, sedative-hypnotic agent and skeletal muscle relaxant. The disclosed invention comprises reacting 3-dimethylamino-1-(3-N-ethyl-N-acetyl-aminophenyl)-2-propen-1-one or a suitable salt thereof with 3-aminopyrazole-4-carbonitrile or a suitable salt thereof in a mixture comprising water and acetic acid or a suitable salt thereof, rather than in acetic acid alone.

11 Claims, No Drawings

PROCESS IMPROVEMENT IN THE SYNTHESIS OF N-[3-(3-CYANO-PYRAZOLO[1,5-A]PYRIMIDIN-7-YL)PHENYL]-N-ETHYLACETAMIDE

This application claims the benefit of U.S. application Ser. No. 60/007,859, filed Dec. 1, 1995, and is a continuation-in-part of that prior application.

BACKGROUND OF INVENTION

The invention is concerned with an improved process for the large scale production of N-[3-(3-cyanopyrazolo[1,5-a]pyrimidin-7-yl)phenyl]-N-ethyl-acetamide which is useful as an anxiolytic, antiepileptic, sedative-hypnotic agent and skeletal muscle relaxant.

PRIOR ART

U.S. Pat. No. 4,626,538 teaches a method of making the desired compound N-[3-(3-cyanopyrazolo[1,5-a]pyrimidin-7-yl)phenyl]-N-ethyl-acetamide, by reaction of 3-dimethylamino-1-(3-N-ethyl-N-acetylaminophenyl)-2-propen-1-one with 3-amino-pyrazole-4-carbonitrile in acetic acid.

DESCRIPTION OF THE INVENTION

It has now been found that improved yields of greater purity can be obtained at decreased reaction times in the formation of N-[3-(3-cyanopyrazolo[1,5-a]pyrimidin-7-yl)phenyl]-N-ethyl-acetamide by adding water to the acetic acid in an amount of about 11% to about 75%(v/v) during the reaction of 3-dimethylamino-1-(3-N-ethyl-N-acetylaminophenyl)-2-propen-1-one or a suitable salt thereof with 3-aminopyrazole-4-carbonitrile or a suitable salt thereof.

In the formation of N-[3-(3-cyanopyrazolo[1,5-a]pyrimidin-7-yl)phenyl]-N-ethyl-acetamide it has unexpectedly been found that a product of extremely high purity and in high yield is obtained by the addition of water to the acetic acid at about 10% to about 85%(v/v). In addition, the reaction times have been significantly decreased from about 3 hours to about 3.5 hours to about 1 hour to about 3.5 hours as well as a reaction temperature decrease from 90° C. to about 25° C. to about 70° C. In contrast, the known prior art methods use acetic acid at reflux temperature (about 120° C.) which produce poor yields and purity because of the formation of contaminates. Unexpectedly, the improved process removed contaminates which often caused the product to be yellowish, thereby giving product which is consistently white, off-white or clear. (Clear product may be obtained initially or upon one recrystallization.)

In the formation of N-[3-(3-cyanopyrazolo[1,5-a]pyrimidin-7-yl)phenyl]-N-ethyl-acetamide it has been found that a suitable range of water in acetic acid is about 10 to about 85%, with 11% to about 75% being preferred and with 60 to 75% (1:2 v/v acetic acid-water) being especially preferred. Preferred embodiments of the present invention utilize about 1:2 v/v acetic acid:-water. When aqueous acetic acid is used according to the present invention, the product is obtained in significantly higher yield and purity than heretofore.

Water may suitably be added to acetic acid at the beginning of the process. Alternatively it may be added to the reaction mixture during the process, in steps or in gradually increasing amounts. One aspect of the invention involves a first addition of water to the reaction mixture at the beginning of the process, followed by a second addition of water once the reaction is substantially complete, e.g. to facilitate the recovery of the product. The amount of water added during the second addition is preferably sufficient to achieve a total of water in acetic acid of about 10% to about 85%, preferably about 11% to about 75% and more preferably about 60% to about 75%. One preferred embodiment of the present invention achieves a total of about 1:2 v/v acetic acid:water.

It would be apparent to a person skilled in the art that the present invention could suitably be performed utilizing acceptable salts of either or both starting materials.

The improvements according to the present invention resulted in a decrease in the reaction time from about 3 hours to about 3.5 hours to 1 hour to about 3.5 hours, a decrease in reaction temperature from 90° C. to about 25° C. to about 70° C. and the production of a product of higher purity which is easily isolated from the one-pot process with a minimum of processing steps. Preferred is a temperature of about 40° C. to about 60° C., more preferred is a temperature of about 50° C. The preferred reaction time is about 1 hour to about 3.5 hours, more preferably about 1 hour to about 2.5 hours or about 1 to 2 hours. The most preferred reaction time is about 1.5 hours. Preferably the yield of product obtained is at least 80% by weight, more preferably at least 84% by weight, most preferably about 85% by weight.

Accordingly, the present invention provides a method of producing the compound designated N-[3-(3-cyanopyrazolo[1,5-a]pyrimidin-7-yl)phenyl]-N-ethyl-acetamide which comprises the reaction of 3-dimethylamino-1-(3-N-ethyl-N-acetylaminophenyl)-2-propen-1-one with 3-aminopyrazole-4-carbonitrile in aqueous acetic acid until said compound is formed and recovering the pure product in improved yields.

The method of the present invention is particularly effective at producing the compound designated N-[3-(3-cyanopyrazolo[1,5-a]pyrimidin-7-yl)phenyl]-N-ethyl-acetamide thereof maintaining said reaction at a preferred temperature of about 25° C. to about 70° C. for a preferred period of about 1 hour to about 3.5 hours and isolating the compounds.

DESCRIPTION OF THE PREFERRED EMBODIMENTS

The following Scheme I illustrates the improved process of the present invention. In Scheme I, 3-dimethylamino-1-(3-N-ethyl-N-acetylaminophenyl)-2-propen-1-one (1) is reacted with 3-aminopyrazole-4-carbonitrile (2) to produce the product N-[3-(3-cyanopyrazolo[1,5-a]pyrimidin-7-yl)phenyl]-N-ethyl-acetamide (3).

SCHEME I

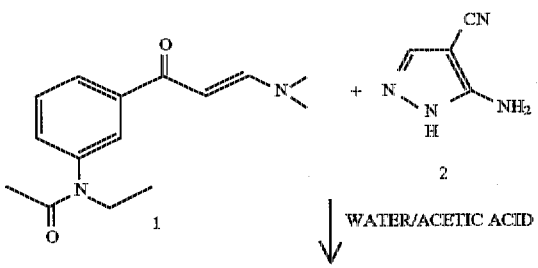

-continued
SCHEME I

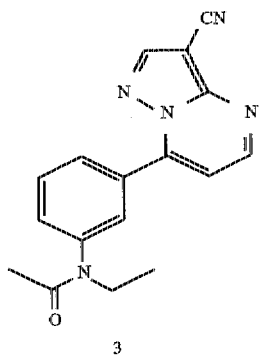

In accordance with Scheme I, 3-dimethylamino-1-(3-N-ethyl-N-acetylaminophenyl)-2-propen-1-one (1) is reacted with 3-aminopyrazole-4-carbonitrile (2) in about 11% to about 75% v/v water:acetic acid. After about 1 hour to about 1.5 hours at about 25° C. to about 70° C. the reaction is complete and the desired product N-[3-(3-cyanopyrazolo[1,5-a]pyrimidin-7-yl)phenyl]-N-ethyl-acetamide (3) is isolated free of contaminates. The product is collected by filtration, washed with water and dried. Use of the above improvements allows preparation of N-[3-(3-cyanopyrazolo[1,5-a]pyrimidin-7-yl)phenyl]-N-ethyl-acetamide (3) in 85% or more overall yield as compared with 76% overall yield obtained using the procedure in Example 14 of U.S. Pat. No. 4,626,538.

In particular, the compound is produced under controlled conditions at a temperature of about 25° C. to about 70° C. for about 1 hour to about 3.5 hours.

The effect of adding water to acetic acid on the preparation of N-[3-(3-cyanopyrazolo[1,5-a]pyrimidin-7-yl)phenyl]-N-ethyl-acetamide (3) is shown in FIG. 1.

As can be seen from FIG. 1 the production of the compound N-[3-(3-cyanopyrazolo[1,5-a]pyrimidin-7-yl)phenyl]-N-ethyl-acetamide is accomplished at lower temperatures in aqueous acetic acid as well as shorter reaction times as compared to the art.

EXAMPLE 1

N-[3-(3-Cyanopyrazolo[1,5-a]pyrimidin-7-yl)phenyl]-N-ethyl-acetimide

A mixture of 315 g of 3-dimethylamino-1-(3-N-ethyl-N-acetylaminophenyl)-2-propen-1-one and 138 g of 3-aminopyrazole-4-carbonitrile in 789 ml of acetic acid and 1500 ml of water is warmed to about 50° C. After about 1–1.5 hours the reaction mixture is cooled to about 5°–15° C. and the crystalline product formed is collected by filtration, washed with water and dried at 60° C. The product is obtained in 86.2% yield and 99.05% area percent pure by HPLC.

EXAMPLE 2

N-[3-(3-Cyanopyrazolo[1,5-a]pyrimidin-7-yl)phenyl]-N-ethyl-acetamide

The following table illustrates the affect of variation of the reaction conditions of Example 1:

TABLE 1

| Expt. | Time, Hr | Temp ° | Moles | Solvs Ratio HAc/H2O | Prod. gr. | Yield % | Hplc Area % Purity. |
|---|---|---|---|---|---|---|---|
| 1 | 1.5 | 50° | 0.04 m | 40/80 ml | 10.2 | 83.5 | 99.4 |
| 2 | 1.5 | 50° | 0.04 m | 30/60 ml | 10.6 | 86 | 99.2 |
| 3 | 1.5 | 50° | 0.04 m | 25/50 ml | 10.3 | 84.5 | 99.06 |
| 4 | 1.5 | 70° | 0.04 m | 40/80 ml | 10.4 | 85 | 98.86 |
| 5 | 1.5 | 50° | .27 m | 269/538 ml | 67 | 81.7 | 99.1 |
| 6 | 1.5 | 70° | 0.27 m | 269/538 ml | 68 | 83 | 98.97 |
| 7 | 1.5 | 50° | 0.4 m | 263/525 ml | 103 | 84 | 99.1 |
| 8 | 1.5 | 70° | 0.4 m | 263/525 ml | 102 | 82.9 | 98.77 |
| 9 | 1.5 | 50° | 0.4 m | 263/500 ml | 106 | 86.7 | 99.2 |
| 10 | 1.5 | 50° | 1.21 m | 789/1500 ml | 318 | 86.2 | 99.05 |
| 11 | 1.5 | 50° | 0.04 m | 40/80 ml | 11 | 90 | 99.29 |
| 12 | 1.5 | 50° | 0.064 m | 40/80 ml | 16.9 | 86.3 | 98.9 |

EXAMPLE 3

N-[3-(3-Cyanopyrazolo[1,5-a]pyrimidin-7-yl)phenyl]-N-ethyl-acetamide

A mixture of 3-dimethylamino-1-(3-n-ethyl-n-acetylaminophenyl)-2-propenyl-1-one (13.02 g, 0.05 m) and 3-aminopyrazole-4-carbonitrile (5.7 g; 0.0527 m) in 37.5 ml of acetic acid and 113 ml of water was heated to 50° C. After about 1.5–2 hours, the reaction mixture was cooled to 10° C.–20° C. and the crystalline product was collected by filtration, washed with water and dried at 60°. The product (13.1 g) was obtained in 85.8% yield and 98.2% area purity by HPLC.

EXAMPLE 4

N-[3-(3-Cyanopyrazolo[1,5-a]pyrimidin-7-yl)phenyl]-N-ethyl-acetamide

A mixture of 3-dimethylamino-1-(3-n-ethyl-n-acetylaminophenyl)-2-propenyl-1-one (13.02 g, 0.05 m) and 3-aminopyrazole-4-carbonitrile (5.6 g; 0.052 m) in 50 ml of acetic acid and 100 ml of water was heated to 25°–28° C. After about 4.5 hours, the reaction mixture was cooled to 7°–10° C., and the crystalline product was collected by filtration, washed with water and dried at 60° C. The product (12.55 g) was obtained in 82.2% yield and 99.1% area purity by HPLC.

The foregoing examples illustrate the preferred means of practicing the invention: namely, reacting 3-dimethylamino-1-(3-N-ethyl-N-acetylaminophenyl)-2-propen-1-one and 3-aminopyrazole-4-carbonitrile with the 3-aminopyrazole-4-carbonitrile in the preferred ratio of acetic acid/water and, thereafter, recovering the crystalline product by simply cooling the reaction mixture.

In the following three examples an alternate means of practicing the invention is shown: namely, reacting 3-dimethylamino-1-(3-N-ethyl-N-acetylaminophenyl)-2-propen-1-one and 3-aminopyrazole-4-carbonitrile with the 3-aminopyrazole-4-carbonitrile in an initial ratio of acetic acid/water greater than ⅓–⅔ (60%–75% water/acetic acid) and adding more water to achieve this ratio before beginning the recovery crystallization.

EXAMPLE 5

N-[3-(3-Cyanoprazolo[1,5-a]pyrimidin-7-yl)phenyl]-N-ethyl-acetamide

A mixture of 3-dimethylamino-1-(3-n-ethyl-n-acetylaminophenyl)-2-propenyl-1-one (2.6 g; 0.010 m) and of 3-aminopyrazole-4-carbonitrile (1.14 g; 0.010 mm) in 12 ml acetic acid and 1.5 ml water was heated to 70° C. After about 2.0 hours, 30 ml of water was added to the reaction fixture and the contents allowed to cool to room temperature (20° C.) over 1 hour. The resulting crystalline product was collected by filtration, washed with water and dried at 60° C. The product (2.55 g) was obtained in 83.5% yield and 97.3% area purity.

EXAMPLE 6

N-[3(3-Cyanopyrazolo[1,5-a]pyrimidin-7-yl)phenyl]-N-ethyl-acetamide

A mixture of 3-dimethylamino-1-(3-n-ethyl-n-acetylaminophenyl)-2-propenyl-1-one (13.02 g, 0.05 m) and 3-aminopyrazole-4-carbonitrile (5.7 g 0.0527 m) in 85 ml of acetic acid and 50 ml of water was heated to 50° C. After about 2.5–3 hours, 108 ml of water was added to the reaction mixture and the contents allowed to cool to 10° C. The resulting crystalline product (12.15 g) was obtained in 76.5% yield and 99.4% area purity. A second crop of product crystals (1.21 g) was collected from the mother liquor after overnight cooling at 5° C., in 7.9% yield of 96.2 area % purity. (The total yield of 15.3 g was an overall yield of 87.2%.)

EXAMPLE 7

N-[3-(3-Cyanopyrazolo[1,5-a]pyrimidin-7-yl)phenyl]-N-ethyl-acetamide

A mixture of 3-dimethylamino-1-(3-n-ethyl-n-acetylaminophenyl)-2-propenyl-1-one (20 g, 0.077 m) and 3-aminopyrazole-4-carbonitrile (9.3 g, 0.086 m) in 60 ml of acetic acid and 18 ml of water was heated to 60° C. After 3.5 hours, 102 ml of water was added to the reaction mixture and the contents allowed to cool slowly over 3 hours to 0° C. The resulting crystalline product collected by filtration, washed with water and dried at 60° C. under vacuum. The product (21 g) was obtained in 88% yield and 99.2% area purity by HPLC.

I claim:

1. A process for producing N-[3-(3-cyanopyrazolo[1,5-a]pyrimidin-7-yl)phenyl]-N-ethyl-acetamide which comprises reacting 3-dimethylamino-1-(3-N-ethyl-N-acetyl-aminophenyl)-2-propen-1-one or a suitable salt thereof with 3-aminopyrazole-4-carbonitrile in a mixture comprising water and acetic acid or a suitable salt thereof.

2. A process as claimed in claim 1 wherein the reaction is carried out in a mixture comprising about 10% to about 85% (v/v) water:acetic acid.

3. A process as claimed in claim 1 wherein the reaction is carried out in a mixture comprising about 11% to about 75% (v/v) water:acetic acid.

4. A process as claimed in claim 1 wherein the reaction is carried out in a mixture comprising about 60% to about 75% (v/v) water:acetic acid.

5. A process as claimed in claim 1 wherein the reaction temperature is about 25° C. to about 70° C.

6. A process as claimed in claim 1 wherein the reaction temperature is about 40° C. to about 60° C.

7. A process as claimed in claim 1 wherein the time for completion of the reaction is about 1 hour to about 3.5 hours.

8. A process as claimed in claim 1 wherein the time for completion of the reaction is about 1 hour to about 2.5 hours.

9. A process as claimed claim 1 wherein the time for completion of the reaction is about 1 to about 2 hours.

10. A process as claimed in claim 1 wherein the reaction is carried in a mixture comprising about 60% to about 75% (v/v) water:acetic acid and the reaction temperature is about 40° C. to about 60° C.

11. A process according to claim 4 wherein the reaction is initially carried out in a mixture comprising less than 60% (v/v) water:acetic acid, and, prior to recovery, water is added to obtain a mixture comprising about 60% to about 75% (v/v) water:acetic acid.

* * * * *